(12) United States Patent
Agaskar

(10) Patent No.: US 8,557,000 B2
(45) Date of Patent: Oct. 15, 2013

(54) COMPLETE LIQUEFICATION OF LIGNOCELLULOSIC AGROWASTE TO FORM LIQUID BIOFUELS

(75) Inventor: Pradyot A. Agaskar, Blacksburg, VA (US)

(73) Assignee: Lignoil Technologies Private Limited, Mumbai (IN)

( * ) Notice: Subject to any disclaimer, the term of this patent is extended or adjusted under 35 U.S.C. 154(b) by 350 days.

(21) Appl. No.: 12/866,350

(22) PCT Filed: Feb. 4, 2009

(86) PCT No.: PCT/IN2009/000076
§ 371 (c)(1),
(2), (4) Date: Aug. 5, 2010

(87) PCT Pub. No.: WO2009/116070
PCT Pub. Date: Sep. 24, 2009

(65) Prior Publication Data
US 2010/0317070 A1 Dec. 16, 2010

(30) Foreign Application Priority Data
Feb. 5, 2008 (IN) .......................... 245/MUM/2008

(51) Int. Cl.
*C10L 1/00* (2006.01)
*C12P 17/04* (2006.01)
*C12P 7/10* (2006.01)
*C12P 7/22* (2006.01)

(52) U.S. Cl.
USPC .............. 44/307; 435/41; 435/317.1; 585/14; 585/242; 585/904

(58) Field of Classification Search
None
See application file for complete search history.

(56) References Cited

U.S. PATENT DOCUMENTS

| 4,470,851 A * | 9/1984 | Paszner et al. ................... 127/37 |
| 7,649,086 B2 * | 1/2010 | Belanger et al. ............. 530/502 |
| 2005/0026262 A1 * | 2/2005 | Yoshitani et al. ............. 435/167 |

OTHER PUBLICATIONS

Hamelinck, Carlos N.; et al; "Ethanol from lignocellulosic biomass; techno-economic performance in short, middle and long-term." Biomass & Energy, 28, 384-410, 2005.*
Onda, Ayumu; et al; "Selective hydrolysis of cellulose into glucose over solid acid catalysts." Green Chemistry, 10, 1033-1037, 2008.*

* cited by examiner

*Primary Examiner* — Blaine Lankford, Jr.
*Assistant Examiner* — David Berke-Schlessel
(74) *Attorney, Agent, or Firm* — George W. Moxon, II; Brian P. Harrod

(57) ABSTRACT

A process for converting lignocellulosic materials which are field residues such as cotton stalks and corn stover, process residues such as sugarcane bagasse and sweet sorghum bagasse, woody parts of energy crops such as switchgrass and miscanthus, forest residues or byproducts of the wood processing industries such as sawdust from sawmills to a liquid biofuel by a series of processing steps wherein the feed materials are hydrolysed in three stages and withdrawn as three product streams each consisting of solubilized fragments of one of the three major components of the feed materials and a set of concurrently operating processing steps wherein each of the three product streams is transformed through chemical or biochemical processes into products, such as pure lignin and ethanol, that have a high calorific value and process wherein these products with high calorific value are combined to form a liquid biofuel.

18 Claims, 3 Drawing Sheets

COMPLETE LIQUEFICATION OF LIGNOCELLULOSIC AGROWASTE TO FORM LIQUID BIOFUELS

BACKGROUND OF THE INVENTION

1. Field of the Invention

The present invention relates to methods and techniques for converting agrowaste biomass which are solid lignocellulosic materials to liquid biofuels with an energy content that is more than 70% of that of the solid agrowastes themselves. More particularly, this invention relates to methods and techniques which in toto comprise the process of achieving this conversion by means of a set of sequential and concurrent processing steps requiring temperatures of between 275 K to 500 K, pressures between 0.1 MPa to 1 MPa and total energy inputs ca. 8 GJ per dry ton of solid agrowaste biomass. Even more particularly, this invention relates to the judicious selection, arrangement and coordinated operation of processing steps, and their constituent unit operations, that result initially in a separation of the solid lignocellulosic materials into fractions consisting essentially of each of the chemical components of such agrowastes viz. 35-50% cellulose, 15-35% hemicellulose, 10-30% lignin, 2-5% extractives and 2-3% ash and subsequently in reformation of the fractionated solid agrowastes and reconstitution to form a liquid biofuel.

2. Description of Prior Art

Processes for converting solid lignocellulosic materials to liquid biofuels have been known and practiced for a relatively long period of time in human history eg the ancient Egyptians carried out wood distillation to produce charcoal, tar and pyroligneous oils.

Wood distillation, wherein the central processing step is pyrolysis which is the technique of applying high heat, ca. 800 K, to lignocellulosic materials in the absence of air, to produce charcoal was a major industry during the 1800s, supplying the fuel for the industrial revolution, until it was replaced by coal. In the late 19th Century and early 20th Century wood distillation with subsequent collection of the condensable off-gases as pyroligneous oils was still profitable for producing soluble tar, pitch, creosote oil, chemicals. The wood distillation industry declined in the 1930s due to the advent of the petrochemical industry. Modern embodiments of this process yield a liquid biofuel product in 60-75% yield containing ca. 35% of the energy contained in the feed material. (cf D. Mohan et al: Energy & Fuels, 2006, 20, 848-889.)

This traditional method was supplemented by a synthetic process developed ca. 1930 which utilizes a pyrolysis reactor operating as a gasifier, ca. 1200 K, by injecting substoichiometric oxygen into the reactor core to partially burn the biomass to ash and reducing gases. After purification the syngas, hydrogen and carbon monoxide in a 2 to 1 ratio, is transformed by catalysts under high pressure and heat, to form methanol. This method produces ca. 100 gallons of methanol per dry ton of feed material containing about 35% of the energy contained in the feed material. Modern variants of this method convert the syngas to other liquid biofuels such as ethanol or hydrocarbons containing ca. 40% of the energy contained in the feed material. (cf. A. P. C. Faaij et al: Biomass & Bioenergy, 2002, 23, 129-152). Another process known since the early 1800s and practiced on a comparatively small scale since the early 1900s prepared ethanol from wood by a sequential series of processing steps (i) Acid Catalyzed Wood Hydrolysis, at around 450 K (ii) Microbial Fermentation and (iii) Distillation (cf E. Boullanger: Distillerie Agricole et Industrielle; Paris: Ballière, 1924). The yield of ethanol was limited to ca. 100 L per dry ton containing ca. 10% of the energy contained in the feed material. Modern embodiments of this process for converting solid lignocellulosic materials to ethanol, particularly involving improvements in the operations of the first step by conducting it in two stages with the second stage being an enzymatic hydrolysis of the cellulose component (cf. USP #33972775 dt. 1976), have enabled an increase in the yield of ethanol to ca. 90 gallons of ethanol containing ca. 40% of the energy contained in the feed material. (cf. P. Zhang: J. Ind Microbiol Biotechnol, 2008, 35, 367-375; C. A. Cardonna et al: Bioresource Tech. 2007, 98, 2415-2497; T. W. Jeffries: Appl. Microbiol. Biotech. 2003, 63, 258-266).

Thus the methods known and practiced in the art to date are limited in the yield of energy contained in the liquid biofuels that are produced from lignocellulosic feed materials, generally in the range 35%-45%.

SUMMARY OF THE INVENTION

1. Objects

It is the object of this invention to increase the yield of energy contained in liquid biofuels produced from lignocellulosic materials such as agrowaste biomass by first isolating the lignin contained in the feed material in a chemically modified form that is soluble in the liquid fuels produced from the sugars contained in the feed material by means that are generally similar to those currently known and practiced in the art. A further object is to achieve this first object in an a priori cost-effective and energy-efficient manner, through judicious selection and combination of processing steps, as for example an appropriate catalyst and catalyst recycling step, such that the only major inputs to the overall process are agrowaste biomass, water and energy in the form of heat and electricity. A yet further object is to provide sufficiently mild processing conditions, viz. temperature and operating pressure in each processing step, so as to reduce the cost of steam and electricity required in these steps and the formation of degradation products having a deleterious effect on the operation of downstream process steps.

2. Advantages

The present invention, by greatly increasing the yield of energy contained in the liquid biofuels produced from lignocellulosic materials, lowers the cost per GJ of energy contained in the liquid biofuels both in terms of capital expenditures required for setting up the processing plants and the operating expenses incurred during the running of these plants. The lower cost liquid biofuel can be used as an economically competitive substitute for liquid fuels derived from petroleum crude. A further reduction in cost per GJ of the liquid biofuel is achieved due to the manner in which the present invention provides streams of the essentially pure components, lignin and cellulose, both of which can be in part processed further to much higher value products and the higher value realization used to offset some of the processing costs entailed for the production of the liquid biofuels themselves.

In light of dwindling reserves of petroleum crude and the increasing atmospheric carbon dioxide levels caused by fossil fuel consumption the energy content of agrowastes represents a very attractive renewable resource that can be utilized as the raw material for the preparation of renewable liquid fuels.

It has been estimated ca. 1000 million tons of agrowaste biomass are produced in the United States of America alone each year, the corresponding figures for China and India are ca. 640 million tons and ca. 545 million tons respectively and for the entire world ca. 4 billion tons annually. The energy content of these agrowastes is thus almost 50% that of the energy content of the petroleum crude used annually in the world and if converted to a liquid biofuel form could reduce the need for petroleum crude by a substantial amount.

While there are traditional uses, mainly as fodder and fuel wood and to some extent as soil conditioners, for these lignocellulosic materials especially in the less developed parts of the world, their energy content is mostly dissipated as a result of natural decay processes or burning in fields being readied for the next planting crop cycle.

Thus an economical, energy efficient and environmentally benign process of converting lignocellulosic materials into liquid biofuels would contribute greatly towards solving one of the most pressing problems facing mankind today.

3. Novel Features

The most notably novel feature of the present invention is the three-stage sequential hydrolysis process wherein each of the major components, hemicellulose, lignin and cellulose, are obtained as separate product streams that can be individually transformed further by concurrent processing steps and ultimately recombined to yield the desired liquid biofuel in ca. 50% yield by weight containing a large portion, >70%, of all of the energy contained in the feed materials. The transformation of the lignin component to a form highly soluble in ethanol, upto 50% by weight, is the key to this novel process.

Another noteworthy novel feature is the processing step that cleanly regenerates the catalyst used in one of the hydrolysis steps and thus makes it possible to avoid the use of any major inputs, such as acids and bases, other than the agrowastes and water.

An additional novel feature is that the three separate hydrolysis processes are all carried out in similar reactors all operating in continuous counter-current mode wherein the solid feed materials enter the top of the reactor through a feeder screw and exit at the bottom of the reactor through an extractor screw while the liquid extractant enters at the bottom of the reactor and exits at the top. This equipment design ensures that the first and second component are almost completely removed before the residual feed material moves to the last hydrolysis stage thus rendering the cellulose component very susceptible to enzymatic hydrolysis.

Figure 1:
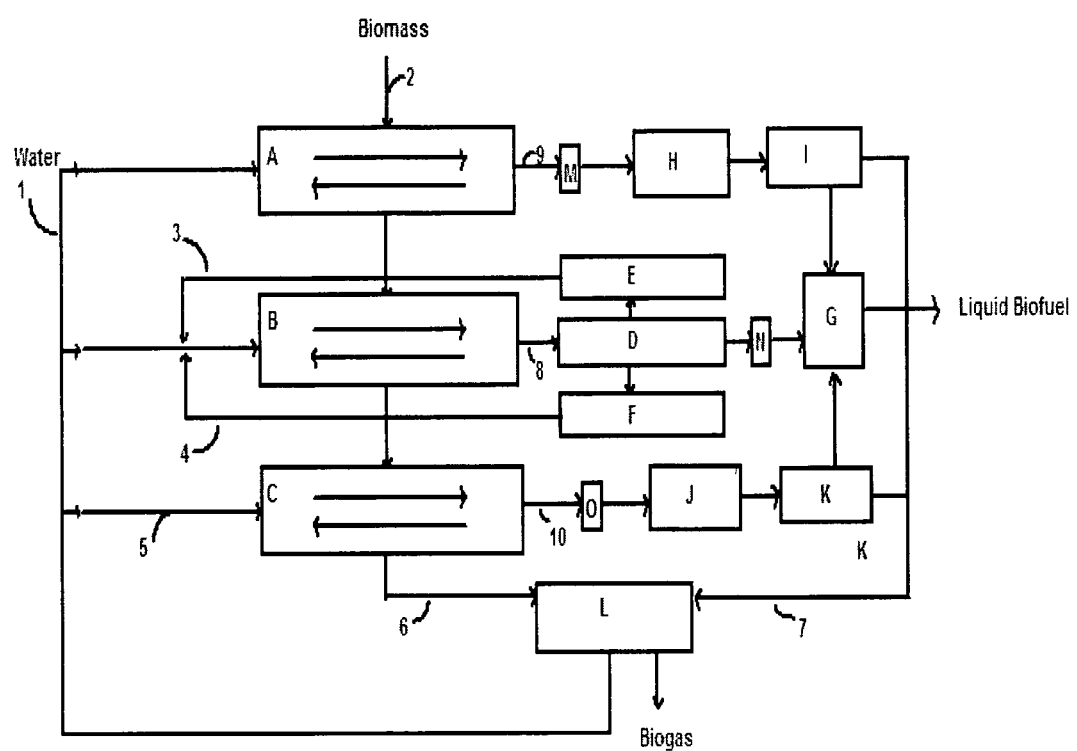
FIG. 1. Process flow diagram showing the sequential processing steps A to C and the concurrent processing steps D to L.

The present invention relates to a process for converting lignocellulosic materials to a liquid biofuel wherein clean, commununted agrowaste biomass 2 along with water 1 is fed into the first digestor A where it is partially hydrolyzed in the first stage of hydrolysis. The liquefied portion, 9 after further processing in M is fed into the fermenter H. The fermented broth is distilled I and the ethanol product fed to the biofuel blender G.

The residual feed material is fed into the second digestor B where it is further hydrolyzed in the second 35 stage of hydrolysis. The liquefied portion 8 is fed to a 3-way separator D from which the solvent is recovered as a vapor E and fed back 3 to the second digestor B along with water 1 and the recycled catalyst 4. The catalyst recovery is accomplished in a pressurized thin film evaporator E. The third faction from the 3-way separator D after further processing N is fed to the biofuel blender G.

The residual feed material enters the third digestor C where it is further hydrolyzed in the third stage of hydrolysis. The liquefied portion 10 after further processing O is fed to the fermenter J. The fermented broth is distilled K and the ethanol product fed to the biofuel blender G.

The portion of the feed material remaining after the third stage of hydrolysis 6 is fed to the biomethanation reactor L along with the effluent from the distillation 7. Water is recovered by reverse osmosis after the biogas production and fed back 1 to the digestors.

Figure 2:
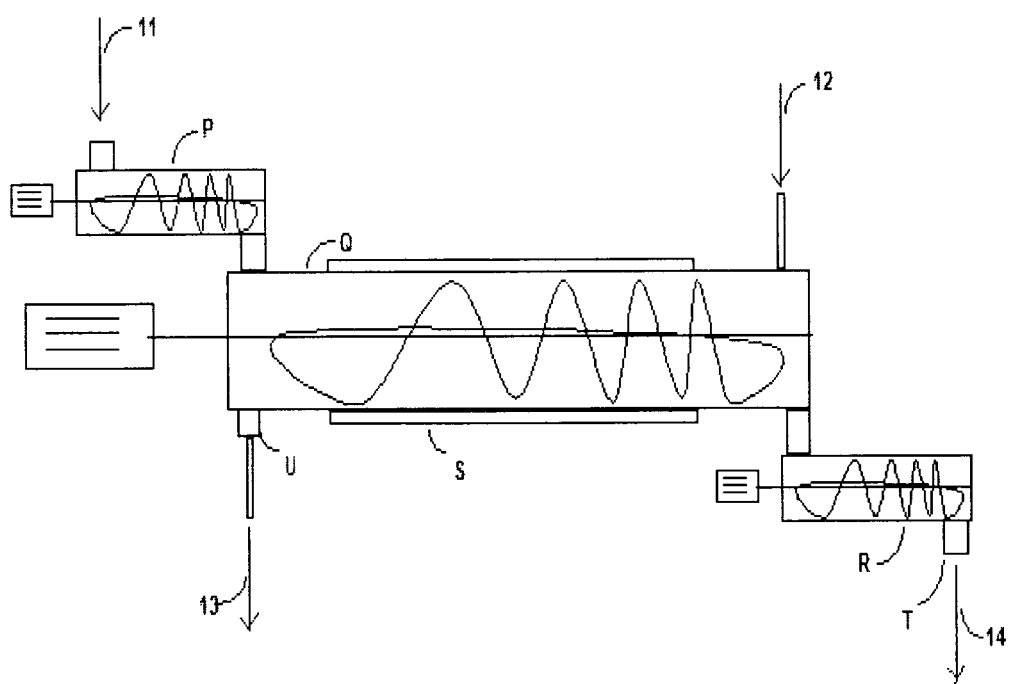

FIG. 2. Digestor assembly consisting of feeder screw, digestor vessel and extractor screw.

Figure 3:
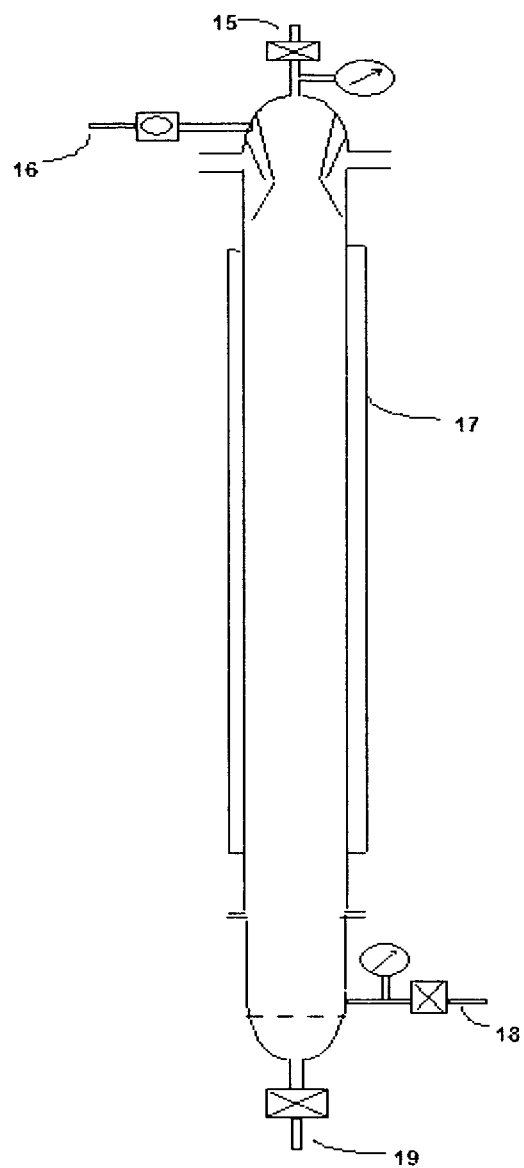

All three stages of hydrolysis are carried out in digestors having a feeder screw P, a digestor Q, heated by a steam jacket R, and an extractor screw, S. Solid feed material 11 is hydrolyzed and the residue 14 is fed to the next digestor in one case through an expansion chamber and sonicator, T. The extractant liquid 12 moves in a countercurrent manner through the digestor and the liquefied product 13 is processed further FIG. 3. Schematic diagram of the pressurized thin film evaporator.

The pressurized thin film evaporator has a long tube 17 with a steam jacket. Steam is fed in through a regulated valve 18 at the bottom and the catalyst solution from the 3-way separator is fed in 16 at the top. Steam is allowed to escape 15 along with decomposition products of contaminants in the catalyst stream. The regenerated catalyst solution is collected 19 and recycled.

DETAILED DESCRIPTION OF THE PREFERRED EMBODIMENT

In processing step A clean agrowaste biomass which has been comminuted using appropriate equipment available for the purpose, such as knife mills, hammer mills and the like is continuously fed via a feeder screw P that compresses it by a factor 6 to 10 into the top of Q where it expands again by imbibing the water that is maintained at ca. 400K by means of a steam jacket S. The water to feed material ratio in the body of Q may be in the range of 3 to 5 and the pressure may be in the range of 0.2 to 0.5 MPa. The feed material moves down the length of Q as a thick slurry at a rate controlled by the rotation of an internal screw and exits through an extractor screw R that compresses it again by a factor of 5 to 10 before expelling it into B.

Water is introduced at the bottom of Q, preferably into the barrel of the extractor screw R and moves up through Q in a countercurrent manner contacting the feed material as it moves down Q. The residence time of the agrowaste biomass in Q may be in the range of 1 to 4 hours during which substantially all of the hemicellulose is dissolved in the water which exits at the top of Q through a filter screen U at a mass flow rate that may be the same as or a small multiple of the mass flow rate of the feed material into Q. As shown in the examples below, almost all of the hemicellulose dissolves in the water and the exiting water stream is a syrup containing upto 35% by weight of the sugar molecules that constitute the hemicellulose component of the feed material. The internal screw may have a gradually decreasing pitch from top to bottom so as to keep the consistency of the slurry constant over the length of the digestor by compensating for the loss of the hemicellulose component of the feed material to the water and a perforated impeller blade to allow countercurrent flow of extractant. The residence time of the extractant viz water in A may be longer than that of the solid agrowaste by a factor determined by the solid to liquid ratio inside Q and the mass flow rate of the exiting extractant 8.

The remainder of the feed material that is injected into B which is also maintained at a temperature ca. 400K by means of a steam jacket S, encounters a countercurrent of an extractant fluid that consists in part of a polar organic solvent that may be methanol, ethanol or acetone and in part water. The design of Q in processing step B is similar to that in processing step A but the material of construction has to be such as to withstand the corrosive effect of the catalyst dissolved in the extractant fluid as an aid to the dissolving action of the extractant fluid on the lignin component of the feed material that is injected into it and also the higher pressure, upto 1 MPa, occasioned by the use of the more volatile organic solvents as part of the extractant fluid. The catalyst may be any strong acid but as shown in the examples below, it is preferably a combination of a metal chloride such as iron(III) chloride and hydrochloric acid present in equimolar proportions. As in processing step A the extractant fluid in processing step B exits Q at the top through a filter screen U at a mass flow rate equal to or a small multiple of the mass flow rate of the feed material entering the digestor at the top. The residence time of the solid in B is ca 1 to 4 hours while the residence time of the extractant fluid is determined by the liquid to solid ratio inside Q and the mass flow rate of the extractant through Q. The salient differences between Q in processing step step A and processing step B are the addition of a recycle loop in the top half of Q so as to ensure an uniform composition of the extractant phase in that half and the multiple points of fluid injection in the bottom half with water being injected into the barrel of the extractor screw R and the organic solvent mixed with the aqueous catalyst solution being injected just below the bottom of the recycle loop. The extractant fluid exiting from the top of B contains almost all of the lignin contained in the feed material that enters B from the bottom of Q via the extractor screw R as shown in the examples appended below. The undissolved solid portion of the feed material, which may be only 35% to 40% by weight of the feed material entering B and consist solely of the cellulose component of the feed material as shown in the examples appended below, is expelled from B by means of an extractor screw R that compresses the slurry exiting the digestor by a factor of 6 to 10 and deposits it in a closed expansion chamber T whose main purpose is to steam strip the remainder of the organic solvent absorbed by the exiting solid but which also serves as the hopper of the feeder screw that compresses it again by a factor of 6 to 10 and deposits it into C. A high-power sonicator may be installed at the entry point of T to mechanically reduce the crystallinity index of the cellulose before it enters C.

C is where the rest of the agrowaste biomass is liquefied by the action of cellulase enzymes and has to be much larger than the first two since the residence time needs to be much longer, up to 24 to 30 hours. The design and construction of C is identical to that of A except for the size as mentioned above. The temperature is maintained at ca. 300K to 325K and pressure is the same as atmospheric pressure. The unsolubilized portion, ca. 10%, of the feed material entering C exits through the extractor screw R as a squeezed, compressed plug and is directed to the effluent treatment unit which may be an anaerobic biomethanation reactor with a reverse osmosis unit attached to the exit end to recover water. The sludge from the biomethanation reactor and the concentrate from the reverse osmosis unit can be sent to an evaporation pond where the solid waste will accumulate and can periodically be collected and sent to a landfill for permanent disposal or can be used as a soil conditioner on arable land.

This sequential train of processing steps will essentially extinguish entirely the feed material flow entering the processing plant and leave very little solid waste to be disposed off in a landfill or used as soil conditioner on arable land.

The three streams 8, 9 and 10 of solubilized components exiting the three digestors may be processed further in concurrently operating processing steps as described below.

The process stream 9 exiting A may contain up to 35% by weight of the sugars constituting the hemicellulose component of the feed material and also acetic acid generated by the hydrolysis of acetyl groups attached to the hemicellulose. This acetic acid may be recovered from the hot effluent stream in an evaporator process unit M and the process fluid may then be passed through an adsorption column 35 to remove the water soluble extractive components of the feed material and finally a column packed with a strong solid acid catalyst such as sulfonated crosslinked polystyrene resin, may be used to hydrolyze oligomeric sugar molecules to their monomeric forms. The process stream containing the monomeric sugar molecules, mainly xylose with varying amounts of the minor components arabinose, galactose, mannose and glucose may then be dropped into fermentor H that has been inoculated with bacteria capable of converting these to ethanol. As is currently known in the art the expected yield of ethanol in fermenter H is ca. 30% by weight of the weight of sugars in the fermentation broth and this may be collected as an azeotropic mixture with water and after being dried in an extractive distillation unit dropped into the lignin solubilization process unit described in detail here. The effluent from the distillation tower may be sent to the effluent treatment unit.

The hot liquid process stream 8 exiting from the top of B which may contain upto 25% by weight of the lignin component first enters a 3-way separation unit where the organic solvent is removed as a vapor which after condensing to a liquid state is recycled to the bottom of the second digestor. The lignin dissolved in the process fluid precipitates as a solid when the organic solvent is removed as a vapor and is collected by means of continuously operating centrifuge unit. The solid is washed with fresh water as it exits the centrifuge unit, dried in a rotary drier and is dropped into the lignin solubilization unit. The third component exiting the 3-way separation process unit is a dilute aqueous solution of sugar molecules and the catalyst in approximately equal amounts, <5% by weight. This may be sent to the top of a pressurized thin film evaporator E wherein the sugar molecules are dehydrated and converted to volatile organic compounds such as furfural and hydroxymethylfurfural, which are removed along with the steam that is generated inside the pressurized thin film evaporator, in a process akin to steam distillation. The strongly acidic process fluid exiting the bottom of the pressurized thin film evaporator may be filtered and recycled to the bottom of B after being mixed with the recovered organic solvent.

The warm process stream 10 exiting C may be passed through column packed with a strongly acidic solid catalyst such as sulfonated crosslinked polystyrene resin, to hydrolyze any glucose oligomers to glucose monomers and dropped into a fermenter J where the glucose monomers are converted to ethanol which may be collected by distillation as an azeotropic mixture with water and after being dried in an extractive distillation unit may be dropped into the lignin solubilization process unit.

The lignin solubilization unit G may be operated in two reactors running in tandem batch mode where the two process streams of ethanol are combined with the dry solid lignin to give a mixture consisting of ca. 40% lignin and 60% ethanol. A solid strong acid catalyst such as sulfonated crosslinked polystyrene resin, may then be added to the mixture, upto 5% by weight, along with some acetone, upto 20% by weight. After stirring for ca. 30 minutes the solubility of lignin increases due to the reaction between lignin and ethanol induced by the catalytic action of the solid acid and the acetone. The reactor is emptied through a filter so as to retain the catalyst in the reactor, the acetone is recovered by distillation and reused and the liquid biofuel sent to the storage tanks.

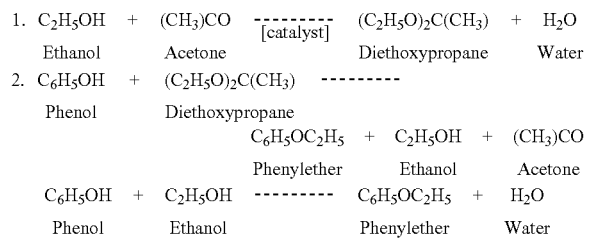

This liquid biofuel has an energy content of ca. 30 MJ/Kg, a density ca. 0.9 g/mL, a kinematic viscosity of ca. 3 cSt and very low sulfur and nitrogen content. It burns cleanly generating no visible soot. It is stable as a liquid and does not solidify even at temperatures below 275 K.

This liquid biofuel may be used for any purpose where there is a need for thermal energy by burning in the presence of air eg an external combustion engine, also called a Stirling Engine, which can convert thermal energy to mechanical energy and thence to electrical energy. Such an arrangement may be carried onboard a moving vehicle powered by batteries and used to recharge the batteries while in motion so as to increase its range.

The present invention is not intended to be limited by the detailed description put forth here and may be embodied in other specific forms without departing from the spirit or essential characteristics of its intended utility as is apparent from the elaboration of the objects of the invention.

EXAMPLES

As an example, the intended objects may be achieved in an embodiment wherein the ethanol component of the liquid biofuel may be obtained by fermentation of the juice obtained by crushing the stalks of the sugarcane plant or sweet sorghum plant and the leftover agrowaste biomass treated as described here with the difference that the hemicellulose sugars obtained in the first digestor would be converted to furfural like molecules in a pressurized thin film evaporator and used as a diesel oxygenate while the glucose obtained from third digestor could be converted to butanol in a fermenter and used as a gasoline additive. The overall yield of liquid biofuels in such an embodiment could reach 16% by weight of the weight of the primary crop, a vast improvement over current state of the art processes.

Example 1

50 Kg of sugarcane bagasse with a moisture content of ca. 10% by weight was mixed with 100 L of water and the mixture was loaded into a 500 L stainless steel pressure vessel fitted a with a steam jacket. The temperature was raised to ca. 400 K when the pressure inside the vessel reached ca. 0.4 MPa. After 4 hours the vessel was cooled and the contents separated into a liquid fraction and a solid fraction using a centrifuge. The solid fraction consisting of the residue of the sugarcane bagasse was washed with 50 L of boiling water twice in succession and then air dried. The dry weight of this fraction was determined to be 31 Kg, 69% by weight. The liquid extract was about 160 L and contained soluble sugars weighing ca. 15 Kg.

Example 2

The sugarcane bagasse residue obtained as described in Example 1 was mixed with 200 L of an extractant liquid consisting of a mixture of equal volumes of water and acetone to which had been added 1.6 Kg of iron(III) chloride and 1 L of a 36% by weight of an aqueous solution of hydrochloric acid. The mixture was loaded into a 500 L stainless steel pressure vessel fitted a with a steam jacket. The temperature was raised to ca. 400K when the pressure inside the vessel reached ca. 0.9 MPa. After 4 hours the vessel was cooled and the contents separated into a liquid fraction and a solid fraction using a centrifuge. The solid fraction consisting of the residue of the sugarcane bagasse was washed first with 50 L of hot acetone and then with 50 L of boiling water and then air dried. The dry weight of this fraction was determined to be 19 Kg, 42% by weight. The liquid extract was about 260 L and the acetone contained therein was recovered by distillation whereupon the lignin precipitated and was collected by filtration. This was found to weigh 8.9 Kg, 20% by weight.

Example 3

The solid lignin obtained in Example 2 was placed in a 50 L round-bottomed flask and 17 L of anhydrous ethanol was added followed by 4 L of acetone. 0.1 Kg of Amberlyst 15 was added and the mixture stirred for 30 minutes until the lignin had dissolved completely. The catalyst was then filtered and the filtrate was bottled.

The invention claimed is:
1. A process for converting lignocellulosic materials to a liquid biofuel comprising lignin dissolved in ethanol produced from cellulosic components, the process comprising:
A) hydrolyzing lignocellulosic feed materials in three concurrent stages including a first stage operated at a temperature of about 400 K that produces a first product stream and a first remainder stream, a second stage operated at a temperature of about 400 K that produces a second product stream and a second remainder stream, and a third stage operated at a temperature of about 400 K that produces a third product stream and a third remainder stream; wherein the first remainder stream is fed into the second stage and the second remainder stream is fed into the third stage, wherein the three product streams are separately withdrawn, and each consists of solubilized fragments selected from the group consisting of hemicellulose components, lignin components, and cellulose components and mixtures thereof,
wherein the hemicellulose component is removed in the first product stream in said first stage and is subjected to fermentation and then distillation to produce ethanol,
wherein the lignin component is removed in the second product stream in said second stage and comprises a mixture of lignin, water, organic solvent vapors selected from methanol, ethanol, and acetone, or mixtures thereof, and catalyst comprising hydrochloric acid and iron (III) chloride, is subjected to filtration to produce a filtrate and a solid lignin component, wherein the lignin is washed with water and dried and the filtrate is passed through a pressurized thin film evaporator at a temperature of about 475 K, whereby volatile organic com- pounds are removed from the liquid stream as a vapor and the catalyst is separated and reused in the second stage, wherein the cellulose component is removed in the third product stream in said third stage wherein the third product stream is subjected to fermentation and then distillation to produce ethanol, and B) combining the processed product streams to recover a product containing lignin and ethanol and having a high calorific value suitable for use as a liquid biofuel.

2. The process of claim 1 wherein the lignocellulosic materials are selected from cotton stalks, corn stover, sugarcane bagasse, sweet sorghum bagasse, switchgrass, miscanthus, and sawdust or mixtures thereof.

3. The process of claim 1 wherein the feed materials are comminuted by mechanical means to a size that passes through at most a 10 mm screen, wherein the comminuted feed materials are compressed such that the volume occupied by a unit weight of the comminuted feed materials is reduced by a factor of 6 to 10 by means of a feeder screw having a variable pitch and dropped into a pressurized digestor vessel for the first stage of hydrolysis.

4. The process of claim 1 wherein the first stage accomplishes greater than 90% removal of the hemicellulose component of the feed material as small fragments soluble in the extractant, wherein said extractant is water, and wherein the small fragments of hemicellulose in the first product stream are further hydrolyzed to form monomers of sugars selected from xylose, arabinose, galactose, mannose and glucose, and mixtures thereof, by passing over a solid strong acid catalyst.

5. The process of claim 1 wherein the first stage is carried out at a pressure of 0.2 to 0.5 MPa for a period lasting from 1 to 4 hours in a pressurized digestor vessel containing the water and the solid feed material in proportions such that the liquid to solid ratio is between 3 and 5 and wherein the mass flow rate of the first product stream is between 2 to 3 times the mass flow rate of the first remainder stream.

6. The process of claim 1 wherein the first remainder stream exits a pressurized digestor vessel through an extractor screw having a variable pitch that compresses it such that the volume occupied by a unit weight of the material is reduced by a factor between 6 and 10.

7. The process of claim 1 wherein the second stages accomplishes greater than 90% removal of the lignin component of the feed material.

8. The process of claim 7 wherein the second stage is carried out inside a pressurized digestor vessel at a pressure between 0.5 MPa and 1.0 MPa for a period lasting from 1 to 4 hours where the ratio of weights of the solid contents and the liquid contents is ca. 4 to 6.

9. The process of claim 7 wherein the ratio of weights of water and organic solvent is in the range of 0.33 to 1.5, wherein the iron (III) chloride catalyst and the hydrochloric acid catalyst are present in equimolar amounts, and wherein the molar amounts of the catalysts are in the range of 0.01 to 0.2 moles for every 1000 g of the water and solvent mixture.

10. The process of claim 8 wherein the mass flow rate of the second product stream is between 2 to 3 times the mass flow rate of the second remainder stream.

11. The process of claim 8 wherein the second product stream is immediately sprayed into a large expansion chamber along with some steam and the organic solvent is completely removed as vapors which are distilled, condensed and reused, wherein the second remainder stream exits the pressurized digestor vessel through an extractor screw having a variable pitch which compresses the feed material to reduce the volume occupied by a unit weight of the feed material by a factor between 6 and 10, wherein residual undissolved feed material exits a digestor vessel through an extractor screw.

12. The process of claim 11 wherein the compressed residual feed material exiting the mouth of the extractor screw enters an expansion chamber, wherein the expansion chamber has a flow of steam through it which collects the vapors of the organic solvent absorbed by the residual feed material and mixes it with the vapors exiting the expansion chamber.

13. The process of claim 12 wherein the expansion chamber also serves as a hopper for a feeder screw that compresses the residual feed material and deposits it into an unpressurized digestor vessel.

14. The process of claim 1 wherein the third stage accomplishes greater than 90% removal of the cellulose component.

15. The process of claim 11 wherein the extractor screw has a variable pitch and compresses the residual feed material such that the volume occupied by a unit weight of the residual feed material is reduced by a factor 6 to 10 before expelling it from the digestor and wherein the third remainder stream is expelled from the unpressurized digestor vessel and dropped into a biomethanation reactor.

16. The process of claim 1 wherein small fragments of cellulose in the third product stream are further hydrolyzed to form glucose monomers by passing over a solid strong acid catalyst.

17. The process of claim 1 wherein all three stages of hydrolysis are carried out in digestors, wherein each digestor is equipped with a screw having a variable pitch that pushes the solid forward and compensates for the loss of mass due to dissolution in the extractant and wherein liquid extractant in all three stages of hydrolysis moves in a countercurrent direction past the solid feed material through perforations in the screw.

18. The process of claim 1 wherein the ethanol is mixed with the solid lignin along with solid strong acid catalyst, wherein the catalyst is filtered off from the mixture after a period ranging from 30 minutes to 1 hour and reused, and wherein the filtrate is sent to a storage tank.

* * * * *